United States Patent
Altarac et al.

(10) Patent No.: US 6,733,502 B2
(45) Date of Patent: May 11, 2004

(54) VARIABLE LOCKING SPINAL SCREW HAVING A KNURLED COLLAR

(75) Inventors: Moti Altarac, Aliso Viejo, CA (US); Philip M. Mellinger, Ladera Ranch, CA (US)

(73) Assignee: Cross Medical Products, Inc., Irvine, CA (US)

( * ) Notice: Subject to any disclaimer, the term of this patent is extended or adjusted under 35 U.S.C. 154(b) by 0 days.

(21) Appl. No.: 10/146,423

(22) Filed: May 15, 2002

(65) Prior Publication Data

US 2003/0216735 A1 Nov. 20, 2003

(51) Int. Cl.$^7$ .............................................. A61B 17/70
(52) U.S. Cl. ........................................ 606/61; 606/73
(58) Field of Search .............................. 606/61, 73, 53, 606/54, 60; 403/90, 274, 284

(56) References Cited

U.S. PATENT DOCUMENTS

| | | | |
|---|---|---|---|
| 4,653,481 A | | 3/1987 | Howland et al. |
| 4,805,602 A | | 2/1989 | Puno et al. |
| 4,913,134 A | | 4/1990 | Luque |
| 5,005,562 A | * | 4/1991 | Cotrel .......................... 606/61 |
| 5,098,432 A | * | 3/1992 | Wagenknecht ............... 606/54 |
| 5,176,678 A | | 1/1993 | Tsou |
| 5,190,543 A | | 3/1993 | Schlapfer |
| 5,207,678 A | | 5/1993 | Harms et al. |
| 5,466,237 A | | 11/1995 | Byrd, III et al. |
| 5,474,555 A | | 12/1995 | Puno et al. |
| 5,480,401 A | * | 1/1996 | Navas .......................... 606/61 |
| 5,562,661 A | * | 10/1996 | Yoshimi et al. ............... 606/61 |
| 5,624,442 A | | 4/1997 | Mellinger |
| 5,738,685 A | * | 4/1998 | Halm et al. ................... 606/61 |
| 5,743,669 A | * | 4/1998 | Fujita et al. ................. 403/131 |
| 6,267,765 B1 | * | 7/2001 | Taylor et al. .................. 606/61 |
| 6,302,883 B1 | * | 10/2001 | Bono .......................... 606/69 |
| 6,554,831 B1 | * | 4/2003 | Rivard et al. .................. 606/61 |
| 6,565,567 B1 | * | 5/2003 | Haider ......................... 606/61 |
| 2003/0069580 A1 | * | 4/2003 | Langmaid et al. ............. 606/59 |

* cited by examiner

*Primary Examiner*—Eduardo C. Robert
*Assistant Examiner*—David Comstock
(74) *Attorney, Agent, or Firm*—Hudak, Shunk & Farine Co. LPA; Laura F. Shunk

(57) ABSTRACT

The invention provides a bone screw for use in an implant assembly having a member including a hole through which the screw extends. The member preferably includes a socket in an anchor that receives a rounded bottom portion of the screw head in order to form a ball and socket connection. The screw has a necked area below the rounded bottom portion which projects through the hole and below that on the longitudinal axis of the screw. The screw includes a knurled collar that is sized so as to allow the anchor to be inserted onto the screw but which subsequently restrains the anchor from falling downward onto the threaded area of the screw.

16 Claims, 2 Drawing Sheets

VARIABLE LOCKING SPINAL SCREW HAVING A KNURLED COLLAR

FIELD OF INVENTION

The invention relates generally to screws for use in a spinal implant system. The particular screw is a fixation screw that can be locked at a variable angle in a stabilizer anchor assembly. The screw includes restraining means that maintains the level of the anchor relative to the longitudinal axis of the screw.

BACKGROUND OF THE INVENTION

Spinal implant systems have been developed for use in addressing certain spinal problems. These systems generally include an elongate stabilizer which is a rod, plate, or cable that is secured to a bone in a stabilizer anchor by means of a fixation member, in this case a screw. In some of these systems, the stabilizer anchor is a separate component from the screw in order to provide for a variable angle of the stabilizer fixation means relative to the angle of fixation. Often for such a system, the components are assembled prior to surgery. The present invention has application for such a system.

These implants have been developed over time to constitute very elegant constructs. The function dictates that the components are relatively easy to assemble and to manipulate and to surgically implant. The design requires minimization of size and invasion into the biological environment, while meeting the structural requirements to achieve the desired function of spinal alignment and stabilization depending on the medical indication. In addition, the construct has to be flexible in its use to account for differences in individuals, or for problems that may arise during the course of surgery. Spine surgery is by its nature intense and long surgery which requires great precision. It is critical that the implements that are developed for use by the surgeon are, given the design considerations, as efficient and easy to use as possible in order to facilitate the surgery.

In a preferred embodiment, the variable angle anchor of the present system can include a concave socket having a central opening through which the screw extends and which captures the convex head of the screw, and transverse to that opening, the anchor includes a channel for the stabilizer which resides above the screw head. Thus, the anchor and the head form a limited ball and socket joint to allow the anchor to have a variable angle on the screw. There can be means to lock the angle at a desired angle. Finally, the system can include means to secure the stabilizer in the anchor. In one particularly elegant design, the securing means can comprise compression means which locks the stabilizer in the anchor and which also locks the position of the anchor relative to the screw. The compression means illustrated with the assembly of the present invention is a nut which is screwed downwardly on external threads of the anchor. When screwed in place, the nut bears down on the stabilizer which in turn compresses the screw head in the anchor to form a locking interface and to lock the angular and radial position of the screw in the anchor. The bottom of the screw includes a machined, high friction surface which improves locking of the screw head in the socket. Of course, it should be understood that other locking or compression means could be used, for example, a locking disc, or a set screw, or other means which use internal threads or flanges on the anchor member.

The particular screw of the present invention is assembled into a cooperation with the stabilizer anchor to permit a variable angle of the anchor with respect to the screw which can subsequently be locked into position at a desired angle as previously discussed. However, the screw presents an advantage over the prior art insofar as the screw includes a restraining means which permits relatively easy assembly of the screw and anchor, but which inhibits the anchor from dropping on the screw to a position which may be difficult for the surgeon to access. The present invention also presents an advantage to variable angle spinal systems which maintain the freedom of movement between the anchor and the screw.

In a preferred embodiment, the restraining means is an annular collar having diamond point knurls which are sized to permit insertion of the screw and collar through the central opening of the anchor member, but where the collar will act to inhibit the anchor from slipping downward on the screw. The anchor actually floats on the screw and moves fairly freely, except the downward play is limited by the interaction of the annular shoulder of the central opening of the anchor and the restraining collar. Preferably at least a relevant portion of the screw head forms a ball and socket type interaction with the anchor opening. Thus, the screw head may include an generally outwardly rounded surface that forms an interface with an inwardly rounded surface of the anchor screw opening. In addition, there is preferably a mating interface between the screw and the anchor in order to ensure a locking cooperation between these two components. This mating interface may for example, be a high friction surface that may be formed as a result of the nature of the mating contoured surfaces, i.e., one surface may be slightly under specification, or alternatively, one or both of the mating surfaces may include a surface which has been worked to render it high friction, such as for example as is the case of the mating diamond point knurls that are shown. Other means of forming this mating locking interface are also contemplated, and include, for example, the use of a locking or pressure disc to effectively increase the frictional fit of the screw head in the socket of the anchor opening.

In the most preferred embodiment, the collar forms an annular barrier below a smooth inwardly rounding portion of the screw head which forms a neck between the screw head and the screw threads. The collar includes two rows of knurls which have a depth of the magnitude of about 0.01 inch and where the collar has a point to point diameter that is approximately the same magnitude larger than the opening in the anchor (or plate) through which it is inserted. This allows the knurls to asymmetrically deform during insertion so as to permit insertion but to inhibit the anchor from slipping below the collar. In the absence of the restraining means, it might be possible for the anchor to slip downward on the screw to a position where it is difficult for the surgeon to reach. This situation could arise for example, where a vertebrae is mis-aligned in the anterior direction, and the screw might not be screwed fully into position. In this instance, the bone surface doesn't act to hold the anchor close to the head of the screw.

OBJECT OF THE INVENTION

It is an object of the invention to provide a bone screw that can be used with a stabilizer including but not limited to a rod or plate or other construct component that is secured to the bone by the screw where the screw includes a restraining collar below the head of the screw in a necked area upward of the screw threads.

It is a further object of the invention to provide a spinal screw that is used in conjunction with a stabilizer anchor where the screw is inserted through an opening in the anchor along the longitudinal axis of the screw, where the screw includes means to inhibit the anchor from slipping longitudinally downward along the screw. In a preferred embodiment, the means to inhibit the downward motion comprises a collar having deformable projections that are collectively close to or slightly larger than the size of the opening in the anchor for the screw to be inserted through. For example, these projections can be diamond point knurls that allow for the screw to be inserted through the opening to the necked portion of the screw, but which maintain the anchor above the collar notwithstanding the fact that the knurls were deformed slightly during assembly with the anchor. Of course, other deformable configurations, such as spiral ridges or splines, or threads could also be used with the collar as the restraining means. Alternately, an asymmetrical opening or key could be used with a corresponding keyway on the collar (or anchor respectively.)

DETAILED DESCRIPTION OF THE INVENTION

Figure 1:
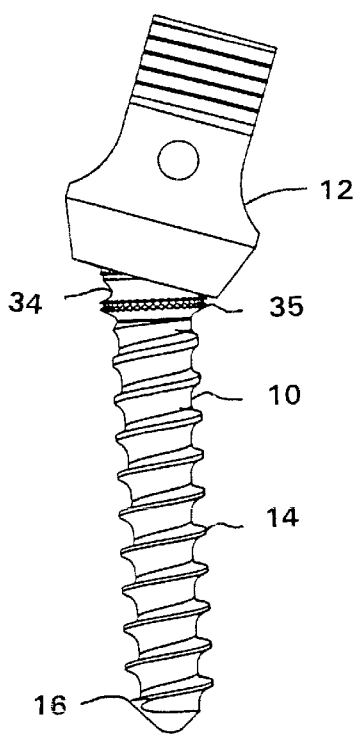
FIG. 1 is a side view of the stabilizer anchor and bone screw assembly in accordance with the present invention.
Figure 2:
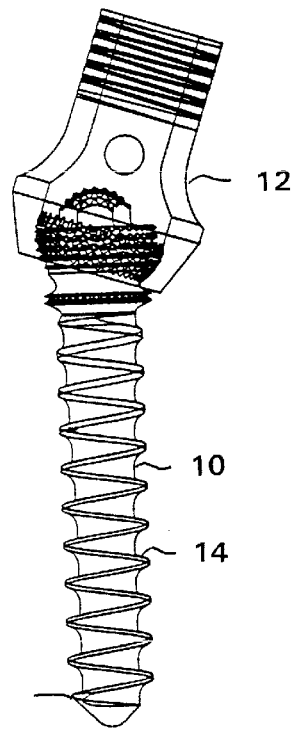
FIG. 2 is cross-section of the assembly of FIG. 1 taken along line 2—2.
Figure 3:
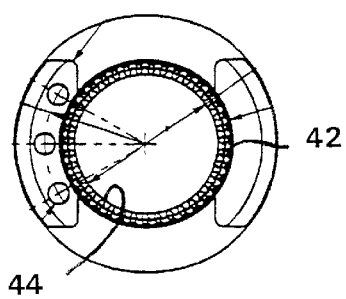
FIG. 3 is a top view of the anchor of FIG. 1.
Figure 4:
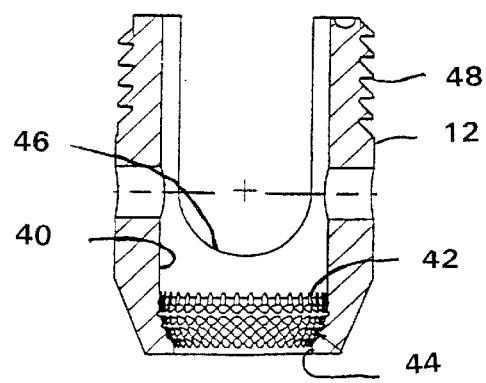
FIG. 4 is cross-section of the anchor of FIG. 1 taken along line 4—4 of FIG. 3.
Figure 5:
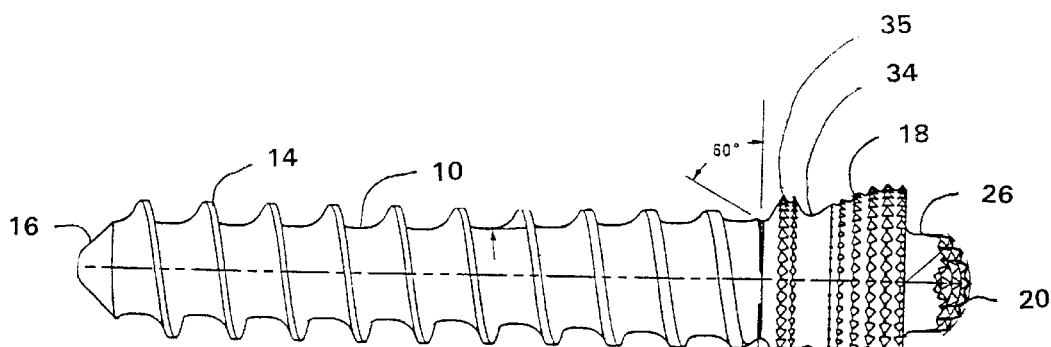
FIG. 5 is a side view of the bone screw in accordance with the invention.
Figure 6:
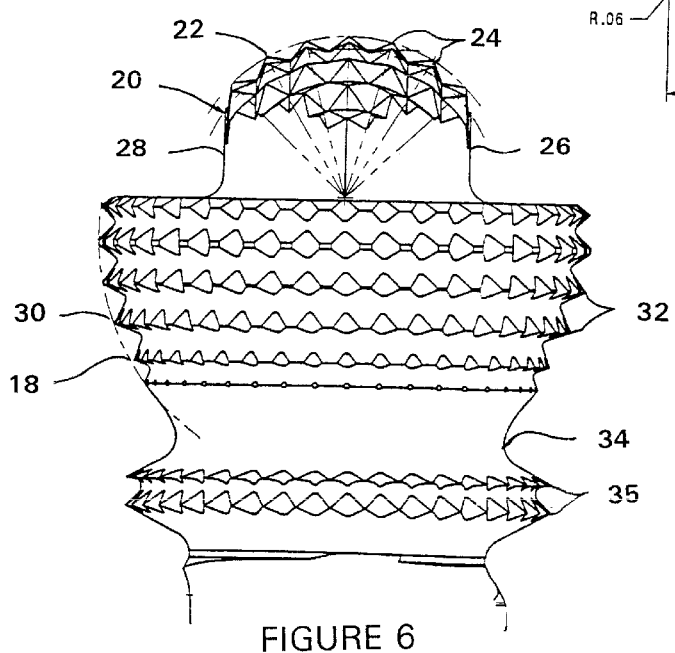
FIG. 6 is a top view of the bone screw of FIG. 5.
Figure 7:
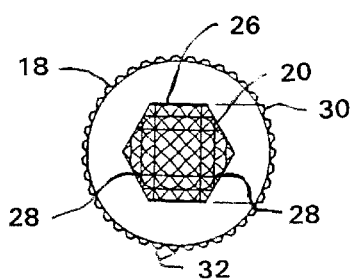
FIG. 7 is a detailed view of the head of the bone screw of FIG. 5.
Figure 8:
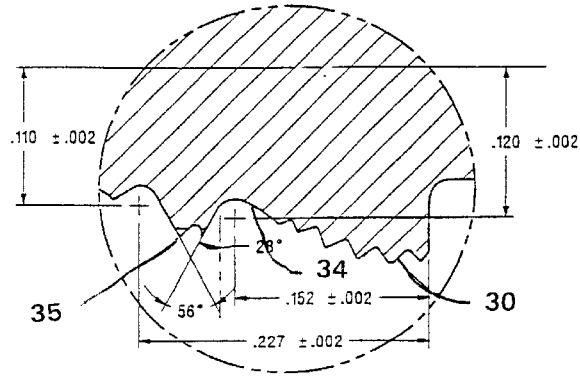
FIG. 8 is a detail in cross-section of the roughened surfaces of the head of the bone screw and of the collar.

FIGS. 1 and 2 show the fixation screw 10 and stabilizer anchor 12 of the present invention. These components are shown assembled. The screw 10 includes a threaded portion 14 for fixation to a vertebral body. The screw has a fluted insertion tip 16 and a complex head 18 which includes a top portion 20 that has a generally outwardly rounded profile that also includes a high friction surface 22, in this case, knurls 24 that contact and bite into the stabilizer. The stabilizer could include a plate or rod, but most likely is a rod if it is used with the anchor member. It is also possible, however, that the screw of the present invention could be used by insertion directly through the bore of a plate member.

The top portion 20 of the screw head 18 includes a torque driving section 26 having a suitable shape, including for example flats 28 which interface with an appropriate torque driving tool. This is shown as an external hexagon, although other shapes could be used, including shapes having complex curves, or even internal torque driving recesses. The screw head includes a bottom portion 30 having a generally outwardly rounded shape that further includes a high friction surface that acts as a means to form a locking interface with the inner surface of the anchor that receives the screw head. This high friction surface is shown as a knurled surface such as for example five rows of diamond point knurls 32. Below the knurled section of the bottom portion 30 there is a smooth necked area 34 that is smaller than the opening of the anchor and extends along the longitudinal axis for about 0.04 to about 0.07 inch. The necked area ends with the collar 35 which forms an angle of about 28° to an axis transverse to the longitudinal axis of the screw. The collar 35 is machined to form two rows of diamond point knurls with an asymmetrical radius between the points of the rows having a radius of about 0.005+/−0.001 with the top points having a sharper edge than the lower points. The bottom side of the collar forms approximately the same angle as the top.

The anchor member 12 includes a socket member 40 having a concavely rounded bottom section 42 that receives and forms a mating interface with the bottom portion 30 of the screw head 18. Preferably, there is a corresponding mating surface in the bottom section of the socket 40 so as to form an interface between the screw head 18 and the socket which locks the angle of the anchor 12 on the screw 10. Of course, it should be understood that other locking means could be used between the screw and the anchor, including for example, other complex curves or binding surface, or pressure or locking disk mechanisms. The socket member includes a terminal opening 44 that defines an annular opening 44 that is slightly smaller than the point to point diameter of the collar 35. For example, the opening may be about 0.005 inch less than the point to point diameter of the collar, and the knurls have a crest to trough height of about 0.01.

Thus as is illustrated in FIGS. 1 and 2, the anchor 12 can pivot on the screw 10. When the anchor is longitudinally aligned with the anchor, the collar acts as a restraining means to inhibit the anchor from slipping fully downward on the screw 10.

In addition, the anchor 12 includes a stabilizer channel 46 which in this case is a U-shaped channel 46 that supports the stabilizer, i.e. the rod, in a position that is transverse to the central opening 44. The anchor 12 also including stabilizer securing means, such as a compression member that screw downward relative to the anchor member 12 to lock the stabilizer in position. In particular, a nut (not shown) may have internal threads that engage external threads 48 on the anchor 12. The anchor also includes a pair of recesses 50 that are used for instrumentation to hold the anchor in place during surgery.

During preparation for surgery, the anchor 12 is fit onto the screw 10 using a special instrument. There is sufficient force to cause the knurls of the collar to deflect or deform to allow the anchor to be fit around the screw. However, the collar still retains the anchor in a loose relation to the screw, and it keeps the anchor from dropping below the collar. However, the screw can still be removed from the anchor using a special instrument. The screw and anchor assembly is fixed to the bone by screwing the screw using the torque-driving shape. A series of such assemblies are implanted. The stabilizer rod can be shaped as desired, inserted into the anchor channels ad locked into place using the securing means. The surgery can include spinal manipulation as is indicated.

While the invention has been discussed with reference to the specific embodiment shown, it should be understood that the bone screw and restraining means of the present invention may have wider application and apply to structure other than just that illustrated.

What is claimed is:

1. An orthopedic implant comprising a bone screw and a member having a through hole which receives the bone screw, the bone screw including threads and a head that is captured in one side of the through hole in the through direction, the head being joined by a necked portion to the rest of the screw, and the screw including a collar which acts as a restraining means for the member having the through hole and is which is located adjacent the necked portion on the opposite side of the through hole from the head.

2. An orthopedic implant as set forth in claim 1 wherein the through hole is circular and has a first diameter, and wherein the collar is annular and has a second diameter and the collar includes teeth having a depth that is about twice the difference between the second diameter and the first diameter.

3. An orthopedic implant as set forth in claim 2 further including a stabilizer and wherein the member is a stabilizer anchor.

4. An orthopedic implant as set forth in claim 3 wherein the stabilizer is a rod, and the stabilizer anchor includes a rod channel which holds the rod in a direction transverse to a plane defined by the circular hole of the stabilizer anchor.

5. An orthopedic implant as set forth in claim 4 wherein the stabilizer anchor further includes means to lock the rod in the rod channel.

6. An orthopedic implant as set forth in claim 5 wherein the means to lock the rod in the rod channel is a compression member which is compressed downward on the stabilizer anchor.

7. An orthopedic implant as set forth in claim 6 wherein the compression member has threads that cooperate with threads on the stabilizer anchor.

8. An orthopedic implant as set forth in claim 7 wherein the compression member is a nut having internal threads that cooperate with external threads on the stabilizer anchor.

9. An orthopedic implant as set forth in claim 1 wherein the screw head has a bottom portion with an outwardly rounded profile and the member includes an inwardly rounded socket that receives the screw head.

10. An orthopedic implant as set forth in claim 9 wherein the screw head includes a top portion including a torque driving area and a rounded portion that interfaces with a stabilizer.

11. An orthopedic implant as set forth in claim 9 wherein at least a portion of the bottom portion of the screw head or of the inside of the socket includes a high friction surface.

12. A spinal implant assembly comprising a rod, a rod anchor and a screw wherein the rod anchor includes a screw socket with a terminal annular opening having a first diameter and transverse to the long axis of the socket, the rod anchor has a rod receiving channel;

and the screw includes a head having a bottom portion that is outwardly rounded and which cooperates with the screw socket and the head includes a necked area that extends through the terminal annular opening to allow the anchor to be positioned at a variable angle relative to the longitudinal axis of the screw on the screw and the screw further includes annular restraining means below the necked portion having a diameter and external configuration so as to allow the screw to be inserted through the annular opening of the rod anchor but which inhibits the anchor from being longitudinally displaced below the restraining means.

13. A spinal implant assembly as set forth in claim 12 wherein the restraining means is a knurled collar.

14. A spinal implant assembly as set forth in claim 13 wherein the rod anchor further includes threaded compression means which locks the rod in position in the channel and the angle of the anchor relative to the screw.

15. A spinal implant assembly as set forth in claim 14 wherein the bottom portion of the screw and the inner portion of the socket include high friction surfaces.

16. A spinal implant as set forth in claim 15 wherein the high friction surfaces are knurled.

* * * * *